(12) United States Patent
Fujikawa et al.

(10) Patent No.: US 9,107,842 B2
(45) Date of Patent: Aug. 18, 2015

(54) MODIFIED HYALURONIC ACID AND/OR A SALT THEREOF, METHOD FOR PRODUCING THE SAME, AND COSMETIC PREPARATION COMPRISING THE SAME

(75) Inventors: Shunichi Fujikawa, Fuchu (JP); Masanori Kurokawa, Hachioji (JP)

(73) Assignee: Kewpie Corporation (JP)

( * ) Notice: Subject to any disclaimer, the term of this patent is extended or adjusted under 35 U.S.C. 154(b) by 189 days.

(21) Appl. No.: 13/579,894

(22) PCT Filed: Feb. 18, 2011

(86) PCT No.: PCT/JP2011/053504
§ 371 (c)(1),
(2), (4) Date: Aug. 17, 2012

(87) PCT Pub. No.: WO2011/102462
PCT Pub. Date: Aug. 25, 2011

(65) Prior Publication Data
US 2012/0316329 A1    Dec. 13, 2012

(30) Foreign Application Priority Data

Feb. 19, 2010 (JP) ................................. 2010-034986
Feb. 19, 2010 (JP) ................................. 2010-034987

(51) Int. Cl.
| | | |
|---|---|---|
| *C08B 37/08* | (2006.01) | |
| *A61Q 19/00* | (2006.01) | |
| *A61K 8/73* | (2006.01) | |
| *A61K 8/34* | (2006.01) | |
| *C08L 5/08* | (2006.01) | |

(52) U.S. Cl.
CPC ................. *A61K 8/345* (2013.01); *A61K 8/735* (2013.01); *A61Q 19/00* (2013.01); *C08B 37/0072* (2013.01); *C08L 5/08* (2013.01)

(58) Field of Classification Search
CPC ...... C08B 37/0072; A61K 8/735; A61Q 19/00
See application file for complete search history.

(56) References Cited

U.S. PATENT DOCUMENTS

| | | | |
|---|---|---|---|
| 5,202,431 A | 4/1993 | della Valle et al. | |
| 5,891,450 A | 4/1999 | Miyajima et al. | |
| 2006/0188465 A1 | 8/2006 | Perrier et al. | |

FOREIGN PATENT DOCUMENTS

| | | |
|---|---|---|
| JP | 06-25306 A | 2/1994 |
| JP | 06-298804 A | 10/1994 |
| JP | 09-235301 A | 9/1997 |
| JP | 2006-312725 A | 11/2006 |

OTHER PUBLICATIONS

Mičochová, Petra, et al., "Preparation and characterization of biodegradable alkylether derivatives of hyaluronan", Carbohydrate Polymers 69, 2007, pp. 344-352.
Extended European Search Report for Application No. EP 11 74 4748 dated Jul. 23, 2013 (6 pages).
The Japanese Pharmacopoeia, 14th edition, 2006, Hirokawa Shoten, Japan. (Partial English translation).
Laurent, Torvard C. et al., "Fractionation of Hyaluronic Acid", Biochimica et Biophysica Acta, 42, 1960, pp. 476-485, Boston, MA, U.S.A. (in English).
English translation of International Preliminary Report on Patentability and Written Opinion for PCT/JP2011053504 mailed Sep. 27, 2012 (7 pages).

*Primary Examiner* — Jonathan S Lau
(74) *Attorney, Agent, or Firm* — Harness, Dickey & Pierce, P.L.C.

(57) ABSTRACT

A modified hyaluronic acid and/or a salt thereof comprises a glycerin skeleton-containing group shown by the following general formula (1),

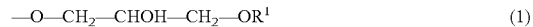

$$-O-CH_2-CHOH-CH_2-OR^1 \qquad (1)$$

wherein, $R^1$ represents a linear or branched alkyl group, or a linear or branched alkenyl group.

16 Claims, 3 Drawing Sheets

(a)

(b)

*: $P < 0.05$ vs AFTER REMOVING CORNEUM

MODIFIED HYALURONIC ACID AND/OR A SALT THEREOF, METHOD FOR PRODUCING THE SAME, AND COSMETIC PREPARATION COMPRISING THE SAME

CROSS-REFERENCE TO RELATED APPLICATIONS

This application is a U.S. National Stage Application of International Application No. PCT/JP2011/053504, filed on Feb. 18, 2011 and published in Japanese as WO/2011/102462 on Aug. 25, 2011. This application claims the benefit of Japanese Application Nos. 2010-034986 and 2010-034987, filed on Feb. 19, 2010. The entire disclosures of the above applications are incorporated herein by reference.

TECHNICAL FIELD

The present invention relates to a modified hyaluronic acid and/or a salt thereof, a method for producing the same, and a cosmetic preparation comprising the same.

BACKGROUND ART

Hyaluronic acid presents widely in living tissues such as cockscombs, umbilical cords, skin, cartilages, vitreous bodies, joint fluid, and is widely used as a component of cosmetics, pharmaceuticals, and foods, for example.

Laid-open Patent Application No. JP 06-25306 describes solvent-insolubilized hyaluronic acid binding to a fatty acid residue to an alcoholic hydroxyl group. However, the solvent-insolubilized hyaluronic acid described in JP 06-25306 has low solubility in both water and ethanol, and thus is not suitable for blending with products containing water or ethanol (e.g., cosmetics, pharmaceuticals, and foods).

SUMMARY OF INVENTION

The present invention provides a modified hyaluronic acid and/or a salt thereof that exhibits an outstanding modified effect to living tissues such as skin, being excellent in water-solubility. The present invention also provides a method for producing the same, and a cosmetic preparation comprising the same.

1. According to one aspect of the invention, there is provided a modified hyaluronic acid and/or a salt thereof comprising a glycerin skeleton-containing group shown by the following general formula (1),

—O—CH$_2$—CHOH—CH$_2$—OR$^1$ (1)

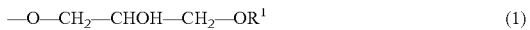

wherein, R$^1$ represents a linear or branched alkyl group, or a linear or branched alkenyl group.

The term "modified hyaluronic acid and/or a salt thereof" used in the invention refers to a hyaluronic acid and/or a salt thereof which an organic group is introduced at least partly therein, having a different structure from the hyaluronic acid and/or a salt thereof. Additionally, the term "organic group" used in the invention refers to a group containing a carbon atom. Further, the term "hydrocarbon group-containing group" used in the invention refers to an organic group containing a hydrocarbon group at least partly. Furthermore, the "hydrocarbon group" of the "hydrocarbon group-containing group" in the "modified hyaluronic acid and/or a salt thereof comprising the hydrocarbon group-containing group" according to the invention differs from a hydrocarbon group contained in the hyaluronic acid and/or a salt thereof.

In addition, the term "glycerin skeleton" refers to a constituent unit shown by —O—CH$_2$—CHOH—CH$_2$—O—. The name "glycerin skeleton" originates from the fact that the glycerin skeleton constitutes a part of glycerin (HO—CH$_2$—CHOH—CH$_2$—OH).

2. In the above modified hyaluronic acid and/or a salt thereof, the R$^1$ in the general formula (1) may be a linear or branched alkyl group which has 6 to 20 carbon atoms, or a linear or branched alkenyl group which has 6 to 20 carbon atoms.

3. In the above modified hyaluronic acid and/or a salt thereof, the glycerin skeleton-containing group may bind to at least one of carbon atoms constituting a hyaluronic acid skeleton.

4. The above modified hyaluronic acid and/or a salt thereof may be obtained by reacting a hyaluronic acid and/or a salt thereof with a compound shown by the following general formula (2),

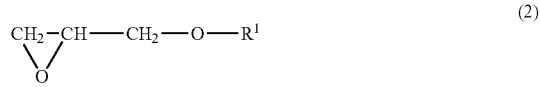

wherein, R$^1$ represents a linear or branched alkyl group, or a linear or branched alkenyl group.

5. In the case of the above 4, the R$^1$ in the general formula (2) may be a linear or branched alkyl group which has 6 to 20 carbon atoms, or a linear or branched alkenyl group which has 6 to 20 carbon atoms.

6. In the above modified hyaluronic acid and/or a salt thereof, a number of the glycerin skeleton-containing group a number of the glycerin skeleton-containing group in one hyaluronic acid constituent unit may be 0.001 to 0.5.

7. In the above modified hyaluronic acid and/or a salt thereof, a kinetic viscosity (1% aqueous solution) of the modified hyaluronic acid and/or a salt thereof may be 50 mm$^2$/s or less.

8. According to another aspect of the invention, there is provided a method for producing the above modified hyaluronic acid and/or a salt thereof comprising reacting a hyaluronic acid and/or a salt thereof with a compound shown by the following general formula (2),

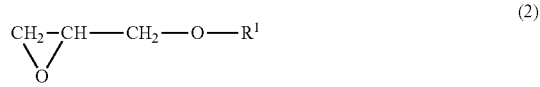

wherein, R$^1$ represents a linear or branched alkyl group, or a linear or branched alkenyl group.

9. According to other aspect of the invention, there is provided a cosmetic preparation comprising the above modified hyaluronic acid and/or a salt thereof.

10. According to other aspect of the invention, there is provided a modified hyaluronic acid and/or a salt thereof comprising a hydrocarbon group-containing group, wherein a transmittance X defined in the following formula (i) is 40% or more, and wherein a transmittance Y defined in the following formula (ii) is 50% or more, $X = T2/T1 \times 100 (\%)$ (i)

wherein, T1 is a transmittance of light having a wavelength of 660 nm and a light path length of 10 mm in water, and T2 is a transmittance of light having a wavelength of 660 nm and a light path length of 10 mm in water comprising 1% of the modified hyaluronic acid and/or a salt thereof comprising the hydrocarbon group-containing group.

$$Y=T4/T3\times100(\%) \quad \text{(ii)}$$

wherein, T3 is a transmittance of light having a wavelength of 660 nm and a light path length of 10 mm in an ethanol-water mixed liquid comprising 70 vol % of ethanol, and T4 is a transmittance of light having a wavelength of 660 nm and a light path length of 10 mm an ethanol-water mixed liquid comprising 70 vol % of ethanol, which comprises 1% of the modified hyaluronic acid and/or a salt thereof comprising the hydrocarbon group-containing group.

11. In the above modified hyaluronic acid and/or a salt thereof, the transmittance X may be 60% or more.

12. In the above modified hyaluronic acid and/or a salt thereof, the transmittance Y may be 70% or more.

13. In the above modified hyaluronic acid and/or a salt thereof, a hydrocarbon group comprised in the hydrocarbon group-containing group may be a linear or branched alkyl group which has 6 to 20 carbon atoms, or a linear or branched alkenyl group which has 6 to 20 carbon atoms.

14. In the above modified hyaluronic acid and/or a salt thereof, a number of the hydrocarbon group-containing group comprised in one hyaluronic acid constituent unit may be 0.001 to 0.2.

15. In the above modified hyaluronic acid and/or a salt thereof, a kinetic viscosity (1% aqueous solution) of the modified hyaluronic acid and/or a salt thereof may be 50 mm$^2$/s or less.

16. According to further other aspect of the invention, there is provided a cosmetic preparation comprising the above modified hyaluronic acid and/or a salt thereof.

Since the above modified hyaluronic acid and/or a salt thereof includes the glycerin skeleton-containing group shown by the above general formula (1), simultaneous pursuit of hydrophilicity and hydrophobicity can be achieved, and thus the above modified hyaluronic acid and/or a salt thereof exhibits excellent modified effect of living tissue such as skin (e.g., repair effect of the skin barrier function) and is excellent in water solubility. Thus, the above modified hyaluronic acid and/or a salt thereof can be used in various products containing water (e.g., cosmetics, foods, and pharmaceuticals), for example, and can exhibits excellent modified effect of living tissue such as skin (e.g., repair effect of the skin barrier function).

DESCRIPTION OF EMBODIMENTS

Figure 1:
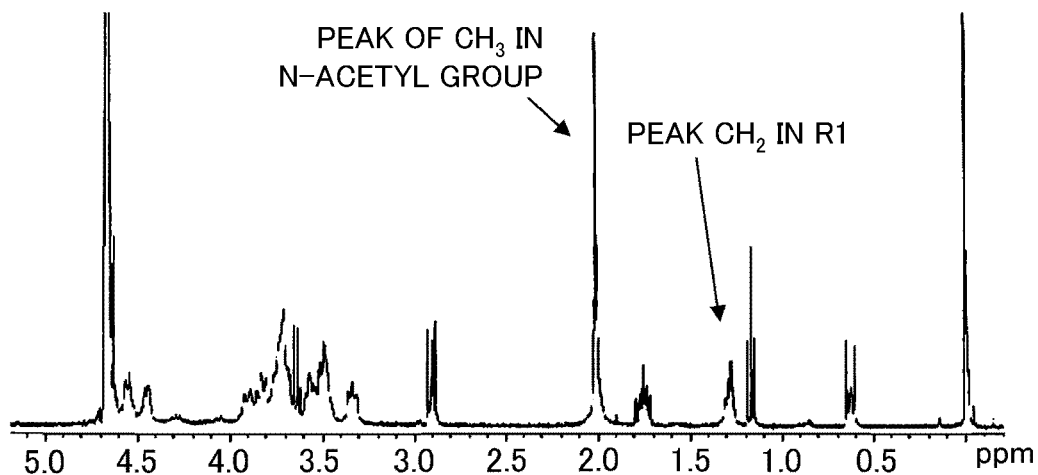
FIG. 1A shows the 1H-NMR spectrum (observing frequency 400 MHz, internal standard substance: DSS (0 ppm), solvent: deuterium oxide) of a modified hyaluronic acid obtained in Example 1.
FIG. 1B shows the 1H-NMR spectrum of a source hyaluronic acid (which does not contain a glycerin skeleton-containing group) (manufactured by Kewpie Corporation, the average molecular weight of 8,000) as a comparative control.
Figure 1:
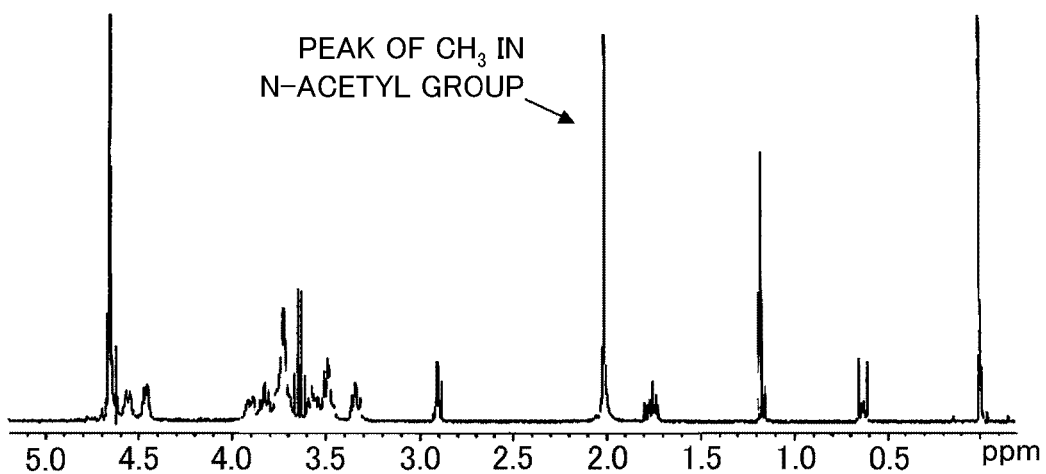

A modified hyaluronic acid and/or a salt thereof, a method for producing the same, and a cosmetic preparation comprising the same according to one embodiment of the invention are described in detail below. Furthermore, in the invention, "%" indicates "mass %" and "part" indicates "mass part".

1. Modified Hyaluronic acid and/or a Salt Thereof 1.1. Structure 1.1.1. Glycerin Skeleton-Containing Group (Hydrocarbon Group-Containing Group)

The modified hyaluronic acid and/or a salt thereof according to this embodiment of the invention comprises a glycerin skeleton-containing group shown by the following general formula (1) (hereinafter referred merely to as "glycerin skeleton-containing group"),

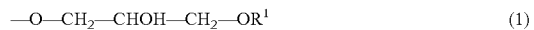

$$-O-CH_2-CHOH-CH_2-OR^1 \quad (1)$$

wherein, R$^1$ represents a linear or branched alkyl group, or a linear or branched alkenyl group.

According to this embodiment modified hyaluronic acid and/or a salt thereof, the R$^1$ in the above general formula (1) binds to one of oxygen atoms which do not constitute hydroxyl groups, the hydroxyl group contained in the glycerin skeleton-containing group is a secondary hydroxyl group, and the other one of the oxygen atoms which do not constitute hydroxyl groups binds to a carbon atom which constitutes hyaluronic acid and/or a salt thereof.

In the general formula (1), the linear or branched alkyl group, which is represented as R$^1$, includes for example, a methyl group, an ethyl group, a n-propyl group, an isopropyl group, a n-butyl group, an isobutyl group, a tert-butyl group, a n-pentyl group, an isopentyl group, a neopentyl group, a tert-pentyl group, a 2-methylbutyl group, a 1-methylbutyl group, a n-hexyl group, an isohexyl group, a 3-methylpentyl group, a 2-methylpentyl group, a 1-methylpentyl group, a n-heptyl group, a n-octyl group, an isooctyl group, a 2-ethylhexyl group, a n-nonyl group, a n-decyl group, a n-undecyl group, a n-dodecyl group, a n-tridecyl group, a n-tetradecyl group (myristyl group), a n-hexadecyl group (palmityl group), a n-octadecyl group (stearyl group), and a n-icosyl group.

Furthermore, in the general formula (1), the linear or branched alkenyl group, which is represented as R$^1$, includes for example, a vinyl group, an allyl group, a propenyl group, an isopropenyl group, a butenyl group, an isobutenyl group, a pentenyl group, an isopentenyl group, a hexenyl group, a heptenyl group, an octenyl group, a nonenyl group, a decenyl group, an undecenyl group, a dodecenyl group, a tetradecenyl group, and an oleyl group.

Of these, in terms of exhibiting more excellent carrier repair effect of the skin and being more excellent in water solubility, the number of the carbon atoms of the linear or branched alkyl group or the linear or branched alkenyl group, which is represented as R$^1$, is preferably 6 to 20, more preferably 8 to 18, and still more preferably 10 to 16. In this instance, an alkyl group is preferred as the group represented by R$^1$.

According to the modified hyaluronic acid and/or a salt thereof of this embodiment, if the number of the carbon atoms of the linear or branched alkyl group or the linear or branched alkenyl group, which is represented as R$^1$, is less than 6, the barrier repair effect of the skin may be inefficient. On the other hand, if the number of the carbon atoms of the linear or branched alkyl group or the linear or branched alkenyl group, which is represented as R$^1$, is more than 20, the water solubility thereof may be low.

1.1.2. Hyaluronic Acid Constitution Unit

The term "hyaluronic acid" used in the invention refers to a polysaccharide including at least one constituent unit consisting of a glucuronic acid and a N-acetylglucosamine. Furthermore, "hyaluronic acid salt thereof (a salt of hyaluronic acid)" is not particularly limited, but preferably a salt being acceptable for food or a pharmaceutically acceptable salt, for example, a sodium salt, a potassium salt, a calcium salt, a zinc salt, a magnesium salt, an ammonium salt, alkyl ammonium salt, an and the like.

Hyaluronic acid is basically disaccharide or polysaccharide, which comprises at least one disaccharide unit combining a C-1 position of a beta-D-glucuronic acid and a C-3 position of a beta-D-N-acetyl-glucosamine, and basically consists of a beta-D-glucuronic acid and a beta-D-N-acetyl-glucosamine, and has more than one of the disaccharide units, and the derivative thereof may include a derivative having a hydrolysable protective group such as an acyl group, for example. The disaccharide or polysaccharide may be an unsaturated sugar, and an example of the unsaturated sugar is a sugar having a non-reducing end, typically, a sugar having an unsaturated bond between a C-4 position and a C-5 position of a glucuronic acid.

According to this embodiment modified hyaluronic acid and/or a salt thereof, a number of the glycerin skeleton-containing group in one hyaluronic acid constituent unit may be preferably 0.001 to 0.5, more preferably 0.005 to 0.2, still more preferably 0.01 to 0.15 in terms of enhancing the repair effect of the skin barrier function further an being more excellent in water solubility. "One hyaluronic acid constituent unit" used in the invention refers to one constituent unit including a disaccharide consisting of glucuronic acid and N-acetyl glucosamine.

According to this embodiment modified hyaluronic acid and/or a salt thereof, if the number of the glycerin skeleton-containing group in one hyaluronic acid constituent unit may be less than 0.001, the solubility in ethanol may be low and the hydrophobicity may not be sufficient, and thus the repair effect of the skin barrier function may not sufficient. On the other hand, if the number of the glycerin skeleton-containing group in one hyaluronic acid constituent unit may be more than 0.5, the solubility in water may be low.

Furthermore, in the modified hyaluronic acid and/or a salt thereof according to this embodiment, the number of the glycerin skeleton-containing group in one hyaluronic acid constituent unit may be identified by 1H-NMR spectrum analysis.

Specifically, the number of the glycerin skeleton-containing group in one hyaluronic acid constituent unit in the modified hyaluronic acid and/or a salt thereof according to this embodiment may be identified by calculating a proportion of an integration value of a peak representing protons in a methylene ($—CH_2—$) group included in the $R^1$ in the glycerin skeleton-containing group to an integration value of a peak representing protons in a methyl group ($—CH_3$) included in $—NHC(=O)CH_3$ (N-acetyl group) in N-acetyl glucosamine constituting one hyaluronic acid constituent unit, in 1H-NMR spectrum of the modified hyaluronic acid and/or a salt thereof according to this embodiment. More specific identification method will be described in Examples of the invention later.

In the modified hyaluronic acid and/or a salt thereof according to this embodiment, the glycerin skeleton-containing group may bind to at least one of carbon atoms constituting a hyaluronic acid skeleton. The term "carbon atoms constituting a hyaluronic acid skeleton" used in the invention refers to carbon atoms included in glucuronic acid and N-acetyl glucosamine which constitute hyaluronic acid. For example, the modified hyaluronic acid and/or a salt thereof may be obtained by reacting at least one of carboxyl groups and hydroxyl groups included in source hyaluronic acid and/or a salt thereof with compound 1 or compound 2 described later to introduce a glycerin skeleton-containing group.

Furthermore, in the modified hyaluronic acid and/or a salt thereof according to this embodiment, the presence of the glycerin skeleton-containing group binding to the modified hyaluronic acid and/or a salt thereof can be identified by a peak representing protons of a methylene group ($—CH_2—$) in the glycerin skeleton-containing group, in comparison of 1H-NMR spectrum of the modified hyaluronic acid and/or a salt thereof according to this embodiment with 1H-NMR spectrum of source hyaluronic acid and/or a salt thereof.

In the modified hyaluronic acid and/or a salt thereof according to this embodiment, the glycerin skeleton-containing group may also bind to at least one selected from a carbonyl group binding to the carbon atom at C-4 position (C-4) and a carbonyl group binding to the carbon atom at C-6 position (C-6), which constitute N-acetylglucosamine of the modified hyaluronic acid and/or a salt thereof, the carbon atom at C-2 position (C-2), the carbon atom at C-3 position (C-3) and a carbonyl group binding to the carbon atom at C-5 position (C-5), which constitute glucuronic acid of the modified hyaluronic acid and/or a salt thereof, for example. Specifically, the modified hyaluronic acid and/or a salt thereof according to this embodiment may be shown in the following general formula (3).

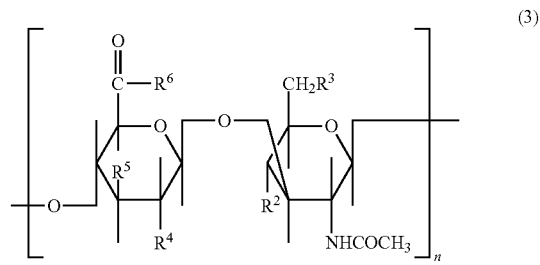

wherein, $R^2$, $R^3$, $R^4$, $R^5$, and $R^6$ independently represent a hydroxyl group or a glycerin skeleton-containing group shown in the above general formula (1) (in this regard, the case that all of the $R^2$, $R^3$, $R^4$, $R^5$, and $R^6$ are a hydroxyl group is excluded), and n represents a number of 1 to 750.)

Furthermore, in the above general formula (3), the hydrogen atom binding to the nitrogen atom in N-acetyl glucosamino group which binds to the carbon atom at C-2 position (C-2) may be substituted with the glycerin skeleton-containing group shown in the above general formula (1).

Also, in the compound shown in the above general formula (3), n may preferably 1 to 50, more preferably 1 to 25 in terms of enhancing the repair effect of the skin barrier function further and being more excellent in water solubility.

1.1.3. Kinetic Viscosity

A kinetic viscosity of the modified hyaluronic acid and/or a salt thereof can be measured using an Ubbelohde viscometer (manufactured by Sibata Scientific Technology Ltd.). In this case, an Ubbelohde viscometer having such a coefficient that the falling time is 200 to 1,000 seconds is selected. The kinetic viscosity is measured in an incubator at 30° C. while maintaining a constant temperature.

The kinetic viscosity ($mm^2/s$) can be calculated by multiplying the falling time (sec) of the aqueous solution measured using the Ubbelohde viscometer by the coefficient of the Ubbelohde viscometer.

The kinetic viscosity of 1% aqueous solution of the modified hyaluronic acid and/or a salt thereof may be preferably 50 mm²/s or less, more preferably 0.1 to 10 mm²/s, still more preferably 0.5 to 3 mm²/s in terms of being more excellent in permeability to the corneum and enhancing the repair effect of the skin barrier function further. If the kinetic viscosity of 1% aqueous solution of the modified hyaluronic acid and/or a salt according to this embodiment is 0.1 to 10 mm²/s (still more preferably 0.5 to 3 mm²/s), the modified hyaluronic acid and/or a salt according to this embodiment, which includes the glycerin skeleton-containing group, can be particularly more excellent in permeability to the corneum and can enhance the repair effect of the skin barrier function much further.

1.1.4. Molecular Weight

The average molecular weight of hyaluronic acid is a value measured by the following method.

Specifically, about 0.05 g of hyaluronic acid is weighed, and dissolved in a 0.2 mol/l sodium chloride solution to prepare a 100 mL of the resulting solution. A 0.2 mol/l sodium chloride solution is added to 8 mL, 12 mL, or 16 mL of the resulting solution to prepare each of the total amounts of 20 mL solutions. The each 20 mL solution and the resulting solution are used as sample solutions. The specific viscosity of each of the sample solutions and a 0.2 mol/l sodium chloride solution are measured at 30.0+−0.1° C. by the viscosity measurement method (first method (capillary viscosity measurement method)) of the general tests of Japanese Pharmacopoeia (14th edition) (expression (A)), and the reduced viscosity at each concentration is calculated (expression (B)). The reduced viscosity (vertical axis) and the dry matter concentration (g/100 mL) (horizontal axis) are plotted on a graph, and the limiting viscosity is calculated from the intersection point of a straight line that connects each point and the vertical axis. The limiting viscosity thus calculated is substituted into the Laurent's formula (expression (C)) to calculate the average molecular weight (Torvard C Laurent, Marion Ryan, and Adolph Pietruszkiewicz, "Fractionation of hyaluronic Acid", Biochemina at Biophysica Acta., 42, 476-485 (1960)).

Specific viscosity=[(falling time of sample solution)/(falling time of 0.2 mol/l sodium chloride solution)]−1  (A)

Reduced viscosity (dL/g)=specific viscosity/(dry matter concentration (g/100 mL))  (B)

Limiting viscosity (dL/g)=3.6×10⁻⁴M⁰·⁷⁸  (C)

M: average molecular weight 1.1.5. Transmittance X, Y

In the modified hyaluronic acid and/or a salt thereof according to this embodiment, a transmittance X of light having a wavelength of 660 nm and a light path length of 10 mm in water containing 1% of the modified hyaluronic acid and/or a salt thereof may be preferably 20% or more (more preferably 40% or more, still more preferably 80% or more) to water. In particular, the modified hyaluronic acid and/or a salt thereof according to this embodiment, which has the above transmittance X of 40% or more in the water containing the modified hyaluronic acid and/or a salt thereof, is excellent in water solubility and is easily blended to products containing water.

In the modified hyaluronic acid and/or a salt thereof according to this embodiment, a transmittance Y of light having a wavelength of 660 nm and a light path length of 10 mm in an ethanol-water mixed liquid (ethanol content: 70 vol %) containing 1% of the modified hyaluronic acid and/or a salt thereof may be preferably 20% or more (more preferably 50% or more, still more preferably 70% or more) to the ethanol-water mixed liquid (ethanol content: 70 vol %). In particular, the modified hyaluronic acid and/or a salt thereof according to this embodiment, which has the above transmittance Y of 50% or more in the above ethanol-water mixed liquid containing the modified hyaluronic acid and/or a salt thereof, is excellent in ethanol solubility, and is easily blended to products containing ethanol, and has high hydrophobicity.

1.2. Method for Producing Modified Hyaluronic Acid and/or a Salt Thereof

The modified hyaluronic acid and/or a salt thereof according to this embodiment is obtained by reacting hyaluronic acid and/or a salt thereof with a compound shown in the following general formula (2) (referred to as "compound 1" herein), for example. Alternatively, the modified hyaluronic acid and/or a salt thereof according to this embodiment may be prepared by reacting hyaluronic acid and/or a salt thereof with a compound shown in the following general formula (4) (referred to as "compound 2" herein). Furthermore, in order to enhance reactivity, substituting a source hyaluronic acid and/or a salt thereof (hereinafter referred to as "source hyaluronic acid and/or a salt thereof") to the alkyl ammonium salt thereof, followed by reacting compound 1 or compound 2 with the alkyl ammonium salt, is preferred.

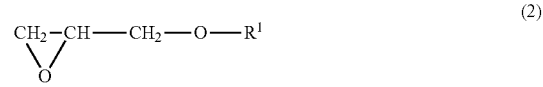

wherein, R¹ represents a linear or branched alkyl group, or a linear or branched alkenyl group.]

The group represented as R¹ in the above general formula (2) may be the groups exemplified as the group represented as R¹ in the above general formula (1).

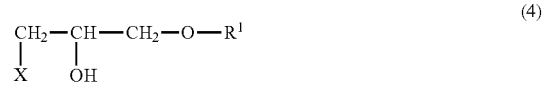

wherein, R¹ is synonymous with the R¹ in the above general formula (2), and X represents a halogen atom.

The halogen atom represented as X in the above general formula (4) may be for example, a chlorine atom, a bromine atom, and an iodine atom.

1.2.1. Source (Raw Material)

Hyaluronic acid and/or salt thereof, which is a source (raw material), may be an extract obtained by extraction from living tissues such as animals (for example, cockscombs, umbilical cords, skin, joint fluid, etc.), or a culture obtained by culturing microorganisms, animal cells, or plant cells (for example, a fermentation method using *Streptococcus* microorganism, and the like), a chemical synthetic, or an enzymatic synthetic can be used.

In general, an average molecular weight of the source hyaluronic acid and/or a salt thereof is preferably 400 to 1,000,000, more preferably 1,000 to 300,000, still more preferably 2,000 to 50,000 in terms of simultaneous pursuit of hydrophilicity and moderate hydrophobicity.

As the source hyaluronic acid and salt thereof used in the invention, the crude extract or the purified product thereof may be used. The purified product thereof with a purity of hyaluronic acid and/or salt thereof of 90% or more is preferred. When using a source hyaluronic acid and salt thereof with a purity of less than 90% as the source, the reaction between the source hyaluronic acid and salt thereof and the compound 1 or the compound 2 may be inhibited, and thus it is not preferred.

1.2.2. Conversion to Alkyl Ammonium Salt

When the source hyaluronic acid and/or a salt thereof is converted to the alkyl ammonium salt thereof, for example, the quaternary alkyl ammonium salt of the hyaluronic acid can be obtained by reacting the source hyaluronic acid and/or a salt thereof with a compound (hereinafter, referred to as "compound 3"). Examples of the compound 3 include for example, a quaternary alkylammonium hydroxide having carbon atoms of 2 to 18 such as tetraethylammonium hydroxide, tetrapropylammonium hydroxide, and tetrabutylammonium hydroxide. Specifically, as the quaternary alkylammonium salt of hyaluronic acid, the quaternary alkylammonium salt having carbon atoms of 2 to 18 is preferred, for example. The quaternary alkylammonium salt includes for example, tetraethylammonium salt, tetrapropylammonium salt, tetrabutylammonium salt, tetrapentylammonium salt, and tetrahexylammonium salt.

1.2.3. Reaction of Alkylammonium Salt with Compound 1 or Compound 2

The reaction of the quaternary alkylammonium salt of hyaluronic acid with the compound 1 or the compound 2 can be performed in an organic solvent. In this case, the reaction temperature is generally 0 to 200° C., and the reaction time is generally 0.1 to 48 hours. The organic solvent used in the above reaction includes for example, dimethylformamide (DMF), dimethylsulfoxide (DMSO), and tetrahydrofuran, and these can be used either individually or in combination with two or more types.

Compound 1 may be used alone or in combination with two or more species. Specific examples of the compound 1 includes for example, an alkyl glycidyl ether such as methyl glycidyl ether, ethyl glycidyl ether, propyl glycidyl ether, butyl glycidyl ether, octyl glycidyl ether, decyl glycidyl ether, dodecyl glycidyl ether, tridecyl glycidyl ether, myristic glycidyl ether, palmityl glycidyl ether, and stearyl glycidyl ether, and an alkenyl glycidyl ether such as allyl glycidyl ether.

Compound 2 may also be used alone or in combination with two or more species. Specific examples of the compound 2 includes for example, methyl 3-chloro-2-hydroxylpropyl ether, ethyl 3-chloro-2-hydroxylpropyl ether, propyl 3-chloro-2-hydroxylpropyl ether, butyl 3-chloro-2-hydroxylpropyl ether, octyl 3-chloro-2-hydroxylpropyl ether, decyl 3-chloro-2-hydroxylpropyl ether, dodecyl 3-chloro-2-hydroxylpropyl ether, tridecyl 3-chloro-2-hydroxylpropyl ether, myristic 3-chloro-2-hydroxylpropyl ether, palmityl 3-chloro-2-hydroxylpropyl ether, stearyl 3-chloro-2-hydroxylpropyl ether, and allyl 3-chloro-2-hydroxylpropyl ether.

1.2.4. Purification The method for producing the modified hyaluronic acid and/or a salt thereof according to this embodiment further includes adding either a sodium salt or a potassium salt to the reaction liquid, followed by reacting hyaluronic acid and/or a salt thereof with compound 1.

The concentration of the sodium salt or the potassium salt in the reaction liquid is preferably 5 to 20%. If the concentration of the sodium salt or the potassium salt is less than 5%, it may be difficult to obtain a precipitate in the following precipitation step. On the other hand, if the concentration of the sodium salt or the potassium salt is more than 20%, the modified hyaluronic acid and/or a salt thereof may precipitate together with the sodium salt or the potassium salt.

Also, the method for producing the modified hyaluronic acid and/or a salt thereof according to this embodiment further includes adding an alcohol to the reaction liquid to obtain a precipitate, followed by adding either a sodium salt or a potassium salt to the reaction liquid. The alcohol includes for example, methanol and ethanol, and ethanol is preferred. In this case, the precipitate is the modified hyaluronic acid and/or a salt thereof. Specifically, modified hyaluronic acid and/or a salt thereof can be obtained by adding the alcohol to the reaction liquid to obtain the precipitate (the modified hyaluronic acid and/or a salt thereof) in order to separate from the remaining reagents.

After obtaining the precipitate, if desired, the precipitate may be washed with a solvent in which the modified hyaluronic acid and/or a salt thereof is slightly soluble (for example, water-containing alcohol). The modified hyaluronic acid and/or a salt thereof can be obtained in a purified form by drying the precipitate subsequently.

The above precipitation step may be performed more than once.

In the method for producing the modified hyaluronic acid and/or a salt thereof according to this embodiment, if the kinetic viscosity of the modified hyaluronic acid and/or a salt thereof is low (for example, having a kinetic viscosity of 10 $mm^2/s$), the precipitate may not be obtained by adding the alcohol to the reaction liquid according to the method described above. In this case, the method for producing the modified hyaluronic acid and/or a salt thereof according to this embodiment can include adjusting the pH of the reaction liquid at 3 or less, followed by adding either a sodium salt or a potassium salt to the reaction liquid, adding a water-soluble organic medium to the reaction liquid having the pH of 3 or less to obtain a suspension, and adjusting a pH of the suspension in a range of 3.5 to 8 to precipitate the modified hyaluronic acid and/or a salt thereof. The modified hyaluronic acid and/or a salt thereof with high purity can be obtained by performing the above reactions, even if the kinetic viscosity is low.

The term "suspension" used in the invention refers to a mixture such that solid particles are dispersed in liquid. For example, the suspension may be opaque liquid in which solids are dispersed, or suspension phase may separate from supernatant phase in the suspension. The suspension phase preferably separates from the supernatant phase since it is easier for the modified hyaluronic acid and/or a salt thereof to precipitate in the subsequent steps.

In the process of obtaining the suspension, the additive amount of the water-soluble organic medium may be a minimum amount required for changing a solution to a suspension, or more. Examples of the water-soluble organic medium are, an alcohol medium such as methanol, ethanol, 1-propanol, 2-propanol, a ketone medium such as acetone, methyl ethyl ketone, tetrahydrofuran, acetonitrile, and the like, and these media may be used either individually or in combination. In particular, ethanol is preferred.

The additive amount of the water-soluble organic medium is preferably one part or more for one part of the solution comprising the hyaluronic acid type, more preferably 2 to 50 parts, still more preferably 5 to 20 parts. In this instance, when the additive amount of the water-soluble organic medium is less than one part for one part of the solution comprising the modified hyaluronic acid and/or a salt thereof, it is a long time before suspension is generated.

Also, in the process of obtaining the suspension, a pH of the solution before adding the water-soluble organic medium is 3 or less, preferably 0.5 to 2.5, more preferably 1 to 2. When the pH of the solution before adding the water-soluble organic medium is more than 3, it is a long time before suspension is generated when the water-soluble organic medium is added, therefore, it is a long time before precipitation of the modified hyaluronic acid and/or a salt thereof occurs when the pH of the solution is adjusted in a range of 3.5 to 8 in the subsequent process. Alternatively, it may be occasionally undesirable in the case that the pH of the solution before adding the water-soluble organic medium is too low, since a large amount of salt is generated at the time of adjusting the pH of the solution in a range of 3.5 to 8 in the subsequent process.

In the method for precipitating the modified hyaluronic acid and/or a salt thereof, the modified hyaluronic acid and/or a salt thereof is precipitated by adjusting the pH of the suspension in a range of 3.5 to 8. In this instance, when the pH of the suspension is out of range of 3.5 to 8, it is difficult to precipitate the modified hyaluronic acid and/or a salt thereof. Also, in terms of accomplishment of higher recovery rate, it is preferable to adjust the pH of the suspension in a range of 4 to 7, more preferably, in a range of 4 to 6.

1.3. Application

The modified hyaluronic acid and/or a salt thereof according to this embodiment exhibits excellent repair effect to living tissues such as skin (particularly, repair effect of the skin barrier function). The modified hyaluronic acid and/or a salt thereof according to this embodiment may be applied to or caused to come in contact with the surface of living tissues, especially, the modified hyaluronic acid and/or a salt thereof according to this embodiment is preferably applied to or caused to come in contact with skin in face, arm, finger, toe, foot, limb, or joint.

As described above, the modified hyaluronic acid and/or a salt thereof according to this embodiment can be used as an ingredient of cosmetics. Specifically, a cosmetic preparation according to this embodiment includes the modified hyaluronic acid and/or a salt thereof. In particular, the modified hyaluronic acid and/or a salt thereof according to this embodiment is excellent in solubility in ethanol. Thus, when the modified hyaluronic acid and/or a salt thereof according to this embodiment are blended to a cosmetic preparation including an oily raw material, the modified hyaluronic acid and/or a salt thereof according to this embodiment and the oily raw material can be mixed without generating separation or precipitation. Accordingly, the modified hyaluronic acid and/or a salt thereof according to this embodiment can be preferably used in a cosmetic preparation including an oil raw material, compared with general hyaluronic acid and/or a salt thereof. The modified hyaluronic acid and/or a salt thereof according to this embodiment has an excellent solubility in water, and thus can be used in various products containing water.

1.4. Effects

Since the modified hyaluronic acid and/or a salt thereof according to this embodiment includes the glycerin skeleton-containing group shown by the above general formula (1), simultaneous pursuit of hydrophilicity and hydrophobicity can be achieved, and thus the above modified hyaluronic acid and/or a salt thereof can exhibit an excellent repair effect of the skin barrier function.

A speculated mechanism of the repair effect of the skin barrier function, which is provided by the modified hyaluronic acid and/or a salt thereof according to this embodiment, is described as follows. Specifically, when the modified hyaluronic acid and/or a salt thereof according to this embodiment is applied to skin, the skeleton portion of the hyaluronic acid, which is in the modified hyaluronic acid and/or a salt thereof according to this embodiment, is disposed in a water layer constituting a corneum of the skin, as well as the glycerin skeleton'-containing group, which is in the modified hyaluronic acid and/or a salt thereof according to this embodiment, is disposed in a lipid layer constituting a corneum of the skin. Accordingly, a lamellar structure including a water layer and a lipid layer, which the skin essentially has, is repaired, and thus the barrier function, which the lamellar structure essentially has, is repaired. Eventually, the repair effect of the skin barrier function can be exhibited.

There is speculation that in the modified hyaluronic acid and/or a salt thereof according to this embodiment, the $R^1$ in the glycerin skeleton-containing group (hydrocarbon group-containing group) may provide hydrophobicity, and hydroxyl groups (including a hydroxyl group in the glycerin skeleton-containing group (hydrocarbon group-containing group)) and/or carboxyl groups may provide hydrophilicity.

When the modified hyaluronic acid and/or a salt thereof according to this embodiment is applied for skin, for example, in a corneum of the skin, the $R^1$ in the glycerin skeleton-containing group (hydrocarbon group-containing group), which is in the modified hyaluronic acid and/or a salt thereof according to this embodiment, penetrates into the lipid layer, as well as the skeleton portion of the hyaluronic acid, which is in the modified hyaluronic acid and/or a salt thereof according to this embodiment, penetrate into the water layer. Accordingly, the lamellar structure of the skin is repaired and water vaporization from the skin can be prevented. Thus, it is considered that moisturizing ability can be enhanced.

Since the modified hyaluronic acid and/or a salt thereof according to this embodiment includes the glycerin skeleton-containing group shown by the above general formula (1), the modified hyaluronic acid and/or a salt thereof according to this embodiment has an excellent solubility in water, and thus can be used in various products containing water, for example.

Since the modified hyaluronic acid and/or a salt thereof according to this embodiment has an excellent solubility in water and ethanol, respectively, and thus when the modified hyaluronic acid and/or a salt thereof according to this embodiment is blended to a product which is water-containing liquid, for example, the modified hyaluronic acid and/or a salt thereof according to this embodiment has an excellent solubility in the product. Eventually, the product with high transparency can be obtained.

1.5. Modified Hyaluronic Acid and/or a Salt Thereof Comprising Hydrocarbon Group-Containing Group The modified hyaluronic acid and/or a salt thereof according to this embodiment may comprise a hydrocarbon group-containing group, and a transmittance X defined in the following formula (1) may be 40% or more, and a transmittance Y defined in the following formula (ii) may be 50% or more.

$$X = T2/T1 \times 100 \, (\%) \quad \text{(i)}$$

wherein, T1 is a transmittance of light having a wavelength of 660 nm and a light path length of 10 mm in water, and T2 is a transmittance of light having a wavelength of 660 nm and a light path length of 10 mm in water comprising 1% of the modified hyaluronic acid and/or a salt thereof comprising the hydrocarbon group-containing group, $$Y = T4/T3 \times 100 \, (\%) \quad \text{(ii)}$$

wherein, T3 is a transmittance of light having a wavelength of 660 nm and a light path length of 10 mm in an ethanol-water mixed liquid comprising 70 vol % of ethanol, and T4 is a transmittance of light having a wavelength of 660 nm and a light path length of 10 mm in an ethanol-water mixed liquid comprising 70 vol % of ethanol, which comprises 1% of the modified hyaluronic acid and/or a salt thereof comprising the hydrocarbon group-containing group.

If the transmittance X of the modified hyaluronic acid and/or a salt thereof according to this embodiment is 40% or more, preferably 60% or more, more preferably 80% or more, the modified hyaluronic acid and/or a salt thereof has excellent solubility in water, and is easily blended to products containing water.

If the transmittance Y of the modified hyaluronic acid and/or a salt thereof according to this embodiment is 50% or more, preferably 70% or more, more preferably 80% or more, the modified hyaluronic acid and/or a salt thereof has excellent solubility in ethanol, and is easily blended to products containing ethanol, and has high hydrophobicity.

In the modified hyaluronic acid and/or a salt thereof according to this embodiment, since the transmittance X is 40% or more (preferably 60% or more, more preferably 80% or more) and the transmittance Y is 50% or more (preferably 70% or more, more preferably 80% or more), simultaneous pursuit of hydrophilicity and hydrophobicity can be achieved, and thus the above modified hyaluronic acid and/or a salt thereof exhibit excellent modified effect of living tissue such as skin (e.g., repair effect of the skin barrier function) and is excellent in water solubility.

The hydrocarbon group-containing group is a group having a hydrocarbon group at least partly. The term "hydrocarbon group" used in the invention refers to a linear or branched alkyl group, or a linear or branched alkenyl group. The linear or branched alkyl group includes for example, a methyl group, an ethyl group, a n-propyl group, an isopropyl group, a n-butyl group, an isobutyl group, a tert-butyl group, a n-pentyl group, an isopentyl group, a neopentyl group, a tert-pentyl group, a 2-methylbutyl group, a 1-methylbutyl group, a n-hexyl group, an isohexyl group, a 3-methylpentyl group, a 2-methylpentyl group, a 1-methylpentyl group, a n-heptyl group, a n-octyl group, an isooctyl group, a 2-ethylhexyl group, an n-nonyl group, a n-decyl group, a n-undecyl group, a n-dodecyl group, a n-tridecyl group, a n-tetradecyl group (myristic group), a n-hexadecyl group (palmityl group), a n-octadecyl group (stearyl group), and a n-icosyl group.

The linear or branched alkenyl group includes for example, a vinyl group, an allyl group, a propenyl group, an isopropenyl group, a butenyl group, an isobutenyl group, a pentenyl group, an isopentenyl group, a hexenyl group, a heptenyl group, an octenyl group, a nonenyl group, a decenyl group, an undecenyl group, a dodecenyl group, a tetradecenyl group, and an oleyl group.

In the modified hyaluronic acid and/or a salt thereof according to this embodiment, the hydrocarbon group-containing group is preferably a group shown in the following general formula (iii), for example, in terms of enhancing the repair effect of the skin barrier function further an being more excellent in water solubility.

(iii)

wherein, $R^1$ represents a hydrocarbon group.

In the modified hyaluronic acid and/or a salt thereof according to this embodiment, for example, if the hydrocarbon group-containing group is the group shown in the above general formula (iii), one of oxygen atoms contained in the —O—$CH_2$—CHOH—$CH_2$—O— portion, which do not constitute a hydroxyl group, binds to the $R^1$, the hydroxyl group contained in the —O—$CH_2$—CHOH—$CH_2$—O— portion is a secondary hydroxyl group, and the other oxygen atom contained in the —O—$CH_2$—CHOH—$CH_2$—O— portion, which do not constitute a hydroxyl group, binds to a carbon atom constituting hyaluronic acid and/or a salt thereof.

In particular, when the hydrocarbon group contained in the hydrocarbon group-containing group (for example, when the hydrocarbon group-containing group is the group shown in the general formula (iii), the hydrocarbon group is the group represented as $R^1$), the number of carbon atoms is preferably 6 to 20, more preferably 8 to 18, and still more preferably 10 to 16, in terms of enhancing the repair effect of the skin barrier function further an being more excellent in water solubility. Furthermore, in this case, the hydrocarbon group contained in the hydrocarbon group-containing group (for example, when the hydrocarbon group-containing group is the group shown in the general formula (iii), the hydrocarbon group is the group represented as $R^1$) is preferably an alkyl group.

In the modified hyaluronic acid and/or a salt thereof according to this embodiment, if the number of the carbon atoms of the hydrocarbon group contained in the hydrocarbon group-containing group (for example, when the hydrocarbon group-containing group is the group shown in the general formula (iii), the hydrocarbon group is the group represented as $R^1$) is less than 6, the repair effect of the skin barrier function thereof may not be efficient. On the other hand, if the number of the carbon atoms of the hydrocarbon group contained in the hydrocarbon group-containing group (for example, when the hydrocarbon group-containing group is the group shown in the general formula (iii), the hydrocarbon group is the group represented as $R^1$) is more than 20, the water solubility thereof may be low.

Since the modified hyaluronic acid and/or a salt thereof according to this embodiment comprises the hydrocarbon group-containing group (for example, the group shown in the above general formula (iii)), the transmittance X of 40% or more, and the transmittance Y of 50% or more, simultaneous pursuit of hydrophilicity and hydrophobicity can be achieved, and thus the above modified hyaluronic acid and/or a salt thereof exhibits excellent repair effect of the skin barrier function. In particular, the modified hyaluronic acid and/or a salt thereof according to this embodiment has excellent solubility in ethanol, and thus has higher hydrophobicity compared with usual hyaluronic acid. Accordingly, the modified hyaluronic acid and/or a salt thereof according to this embodiment can be used in products with high oil content. Additionally, the modified hyaluronic acid and/or a salt thereof according to this embodiment comprises the hydrocarbon group-containing group (for example, the group shown in the above general formula (iii)), the transmittance X of 40% or more, and the transmittance Y of 50% or more, simultaneous pursuit of hydrophilicity and hydrophobicity can be achieved, and thus the modified hyaluronic acid and/or a salt thereof exhibits excellent repair effect of the skin barrier function, as well as being excellent in water solubility. Accordingly, the modified hyaluronic acid and/or a salt thereof can be easily used by blending the modified hyaluronic acid and/or a salt thereof to various products containing water.

2. Cosmetic Preparation

A cosmetic preparation according to one embodiment comprises the above, modified hyaluronic acid and/or a salt thereof. For example, the cosmetic preparation may comprise the above modified hyaluronic acid and/or a salt thereof as a moisturizer. In general, the cosmetic preparation may also comprise the above modified hyaluronic acid and/or a salt of 0.001 to 5%. If the content is less than 0.001%, efficient moisturizing effect and smoothness are not obtained, and thus dry feeling of the skin in use may not be alleviated. On the other hand, the content is more than 5%, the viscosity is too high, and thus spreading the above modified hyaluronic acid and/or a salt thereof on the skin entirely may become difficult. Further, when the cosmetic preparation according to this embodiment is a water-containing liquid, since the cosmetic preparation comprises the modified hyaluronic acid and/or a salt thereof according to this embodiment, which is excellent in water and ethanol, the cosmetic preparation according to this embodiment is highly transparent.

Aspects of the cosmetic preparation according to this embodiment are not particularly limited, but for example, a skin cosmetic preparation. When the above modified hyaluronic acid and/or a salt thereof is used for the skin cosmetic preparation, moderate viscosity is provided, and repair effect of the skin barrier function is high, and thus moisture can be provide to the skin, touch can be improved, and a dry feeling of the skin can be alleviated. Aspects of the skin cosmetic preparation according to this embodiment includes for example, a facial wash, a cleansing preparation, a lotion (for example, whitening lotion), cream (for example, vanishing cream and cold cream), milky lotion, essence, pack (for example, jellied pack, wipe-off-type pasty pack, and rinse-type powdery pack), a cleansing product, foundation, rouge, lip balm, lip gloss, a lip liner, cheek rouge, after-shave lotion, after-sun lotion, deodorant lotion, body lotion (including hand care lotion and foot care lotion), body oil, soap, and bath additive.

The modified hyaluronic acid and/or a salt thereof according to this embodiment has not only excellent solubility in ethanol, but also moderate hydrophobicity. Therefore, when the modified hyaluronic acid and/or a salt thereof according to this embodiment is blended to a cosmetic preparation containing an oily raw material, the modified hyaluronic acid and/or a salt thereof according to this embodiment can be mixed with the oily raw material successfully without generating separation or precipitation. Accordingly, the cosmetic preparation is suitable for a cosmetic preparation containing an oily raw material, such as cream, milky lotion, essence, pack, rouge, lip balm, lip gloss, lip liner, oil cleansing product, foundation, eye shadow, eye liner, for example.

Since the cosmetic preparation according to this embodiment comprises the modified hyaluronic acid and/or a salt thereof, an excellent moisturizing effect can be exhibited.

Additionally, since the cosmetic preparation according to this embodiment comprises the modified hyaluronic acid and/or a salt thereof, the viscosity is adjusted to a moderate degree, and thus dry feeling of the skin can be alleviated.

Accordingly, since the cosmetic preparation according to this embodiment comprises the modified hyaluronic acid and/or a salt thereof, moisture can be provided to the skin, and dry feeling of the skin can be alleviated, for example.

The cosmetic preparation according to this embodiment may further comprise the following ingredients. The ingredients includes for example, a cationized polysaccharide (e.g., cationized hyaluronic acid, cationized hydroxyethyl cellulose, cationized guar gum, cationized starch, cationized locust bean gum, cationized dextran, cationized chitosan, and cationized honey), an anionic surfactant (e.g., alkylbenzenesulfonate, polyoxyalkylenealkylether sulfate salt, alkyl sulfate ester salt, olefin sulfonate, fatty acid salt, and dialkylsulfosuccinate salt), a nonionic surfactant (e.g., polyoxyethylene fatty acid ester and polyoxyethylene hydrogenated castor oil derivative), a cationic surfactant (e.g., alkyltrimethylammonium salt, dialkyldimethylammonium salt, alkylpyridinium salt, and stearyltrimethylammonium chloride), an amphoteric surfactant (e.g., alkyl betaine, alkylamide propyl betaine, imidazolinium betaine, egg-yolk lecithin, and soybean lecithin), oils (e.g., silicone, silicone derivatives, liquid paraffin, squalane, yellow bees wax, carnauba wax, olive oil, avocado oil, camellia oil, jojoba oil, and horse oil)), a moisturizer (e.g., sodium hyaluronate, hydrolyzed hyaluronic acid, acetylated hyaluronic acid, dimethylsilanol hyaluronate, ceramide, lauroyl glutamate diphytosteryloctyldodecyl, phytoglycogen, hydrolyzed eggshell membrane, trehalose, glycerol, atelocollagen, sorbitol, maltitol, and 1,3-butylene glycol), a higher fatty acid (e.g., lauric acid, behenic acid, palmitic acid, stearic acid, isostearic acid, and oleic acid) a higher alcohol (e.g., cetyl alcohol, stearyl alcohol, behenyl alcohol, isostearyl alcohol, and batyl alcohol), a polyhydric alcohol (e.g., glycerol, diglycerol, 1,3-propanediol, propylene glycol, polyethylene glycol, and pentylene glycol), a thickener (e.g., cellulose ether, carboxyvinyl polymer, xanthan gum, and dextrin palmitate), an amphoteric polymer resin compound (e.g., betaine dialkylaminoalkyl acrylate copolymer), a cationic polymer resin compound (e.g., cationized vinylpyrrolidone/dimethylaminoethyl methacrylate copolymer and polydimethyldiallylammonium halide cationic polymer), a preservative (e.g., methylparaben, ethylparaben, butylparaben, propylparaben, and phenoxyethanol), an antioxidant (e.g., tocopherol and BHT), a sequestering agent (e.g., edetate and etidronic acid salt), a UV absorber (e.g., benzophenone derivative, p-aminobenzoic acid derivative, and methoxycinnamic acid derivative), a UV reflection agent (e.g., titanium oxide and zinc oxide), a protein hydrolyzate (e.g., keratin peptide, collagen peptide, soybean peptide, wheat peptide, milk peptide, silk peptide, and egg white peptide), an amino acid (e.g., arginine, glutamic acid, glycine, alanine, hydroxyproline, cysteine, serine, and L-theanine), a natural extract (Sophorae radix extract, chamomile extract, seaweed extract, eucalyptus extract, royal jelly extract, *Rosmarinus officinalis* L. extract, and beech extract), other functional components (coenzyme Q10, arbutin, polyquarternium-51, elastin, platinum nanocolloid, retinol palmitate, panthenol, allantoin, sodium lysine dilauroyl glutamate, magnesium ascorbyl phosphate, L-ascorbic acid 2-glucoside, ellagic acid, kojic acid, linoleic acid, and tranexamic acid), a phospholipid polymer, essence, and a dye.

3. Examples

The invention is further described below by way of examples. Note that the invention is not limited to the following examples.

3.1. Test Method 3.1.1. Average Molecular Weight

In this example, an average molecular weight of (modified) hyaluronic acid was measured by the method described in the above embodiment.

3.1.2. Number of (N) Glycerin Skeleton-Containing Groups (Hydrocarbon Group-Containing Group) or Palmitoyl Groups Contained in One Constitution Unit of Hyaluronic Acid In this example, an integration value of a peak representing protons of methyl group ($-CH_3$) of $-NHC(=O)CH_3$ (N-acetyl group) which constitutes N-acetyl glucosamine, observed at about 2.0 ppm and an integration value of a peak representing protons of methylene group ($-CH_2-$) contained in $R^1$ of glycerin skeleton-containing group or palmitoyl group, observed at about 1.3 ppm are calculated, and then the number of glycerin skeleton-containing groups or palmitoyl groups contained in one constitution unit of hyaluronic acid (referred to as "N" in Table 1) in modified hyaluronic acid is calculated from the integration values based on the following formula (5) to (9).

When the modified hyaluronic acid comprises a glycerin skeleton-containing group having the $R^1$ which is a n-dodecyl group or a n-tridecyl group (test numbers 2 to 10 in Table 1)

Furthermore, in this case, the number of the carbon atoms in the glycerin skeleton-containing group represented as $R^1$ was calculated to 12.5, which is the average number of the carbon atoms in a n-dodecyl group and the carbon atoms in a n-tridecyl group (the number of the carbon atoms in a n-dodecyl group is 12, and the number of the carbon atoms in a n-tridecyl group is 13). Additionally, in this case, the peak appearing at about 1.3 ppm corresponds to 19 hydrogen atoms in total, based on a comparison with the integration value of the peak appearing at about 1.3 ppm to the integration value of hydrogen atoms of $CH_3$ in N-acetyl group, and the 19 hydrogen atoms is considered be 9.5 (the number of methylene groups in $R^1$=—$CH_2$—$CH_2$—$(CH_2)_{9.5}$—$CH_3$)×2 hydrogen atoms. Accordingly, the number of the glycerin skeleton-containing groups contained in one constitution unit of hyaluronic acid is calculated, based on the following formula (5).

The number of the glycerin skeleton-containing groups contained in one constitution unit of hyaluronic acid=(integration value of the peak at about 1.3 ppm/19)/(integration value of the peak at about 2.0 ppm/3)  (5)

When the modified hyaluronic acid comprises a glycerin skeleton-containing group having the $R^1$ which is a n-butyl group (test number 1 in Table 1)

Furthermore, when the $R^1$ is a n-butyl group having 4 carbon atoms, the peak appearing at about 1.3 ppm corresponds to 2 hydrogen atoms in total, based on a comparison with the integration value of the peak appearing at about 1.3 ppm to the integration value of hydrogen atoms of $CH_3$ in N-acetyl group, the 2 hydrogen atoms is considered to be 1 (the number of methylene groups in the parentheses of $R^1$=—$CH_2$—$CH_2$—$(CH_2)_1$—$CH_3$)×2 hydrogen groups. Accordingly, the number of the glycerin skeleton-containing groups contained in one constitution unit of hyaluronic acid is calculated, based on the following formula (6).

the number of the glycerin skeleton-containing groups contained in one constitution unit of hyaluronic acid=(integration value of the peak at about 1.3 ppm/2)/(integration value of the peak at about 2.0 ppm/3)  (6)

When the modified hyaluronic acid comprises a glycerin skeleton-containing group having the $R^1$ which is a palmityl group (test number 11 in Table 1)

Furthermore, when the $R^1$ is a palmityl group having 16 carbon atoms, the peak appearing at about 1.3 ppm corresponds to 26 hydrogen atoms in total, based on a comparison with the integration value of the peak appearing at about 1.3 ppm to the integration value of hydrogen atoms of $CH_3$ in N-acetyl group, the 26 hydrogen atoms is considered to be 13 (the number of methylene groups in the parentheses of $R^1$=—$CH_2$—$CH_2$—$(CH_2)_{13}$—$CH_3$)×2 hydrogen groups. Accordingly, the number of the glycerin skeleton-containing groups contained in one constitution unit of hyaluronic acid is calculated, based on the following formula (7).

the number of the glycerin skeleton-containing groups contained in one constitution unit of hyaluronic acid=(integration value of the peak at about 1.3 ppm/26)/(integration value of the peak at about 2.0 ppm/3)  (7)

When the modified hyaluronic acid comprises a glycerin skeleton-containing group having the $R^1$ which is a stearyl group (test number 12 and 13 in Table 1)

Furthermore, when the $R^1$ is a stearyl group having 18 carbon atoms, the peak appearing at about 1.3 ppm corresponds to 30 hydrogen atoms in total, based on a comparison with the integration value of the peak appearing at about 1.3 ppm to the integration value of hydrogen atoms of $CH_3$ in N-acetyl group, the 30 hydrogen atoms is considered to be 15 (the number of methylene groups in the parentheses of $R^1$=—$CH_2$—$CH_2$—$(CH_2)_{15}$—$CH_3$)×2 hydrogen groups. Accordingly, the number of the glycerin skeleton-containing groups contained in one constitution unit of hyaluronic acid is calculated, based on the following formula (8).

the number of the glycerin skeleton-containing groups contained in one constitution unit of hyaluronic acid=(integration value of the peak at about 1.3 ppm/30)/(integration value of the peak at about 2.0 ppm/3)  (8)

When the modified hyaluronic acid does not comprise a glycerin skeleton-containing group but comprise a palmitoyl group (test number 14 and 15 in Table 1)

Furthermore, in the case of the palmitoyl group, the peak appearing at about 1.3 ppm corresponds to 24 hydrogen atoms in total, based on a comparison with the integration value of the peak appearing at about 1.3 ppm to the integration value of hydrogen atoms of $CH_3$ in N-acetyl group, the 24 hydrogen atoms is considered to be 12 (the number of methylene groups in the parentheses of the palmitoyl group, —C(=O)—$CH_2$—$CH_2$—$(CH_2)_{12}$—$CH_3$)×2 hydrogen groups. Accordingly, the number of the palmitoyl groups contained in one constitution unit of hyaluronic acid is calculated, based on the following formula (9).

the number of the palmitoyl groups contained in one constitution unit of hyaluronic acid=(integration value of the peak at about 1.3 ppm/24)/(integration value of the peak at about 2.0 ppm/3)  (9)

3.1.3. Transmittance X, Y

The modified hyaluronic acid obtained in each example was added to water and ethanol-water mixed liquid (ethanol content: 70 vol %), respectively to prepare water containing 1% of modified hyaluronic acid and ethanol-water mixed liquid containing 1% of modified hyaluronic acid, respectively. Next, transmittance X,Y of light having a wavelength of 660 nm and a light path length of 10 mm were measured with using a spectrophotometer, brand name "spectrophotometric UV-2450" manufactured by SHIMADZU CORPORATION.

3.1.4. Kinetic Viscosity

Kinetic viscosity was calculated in accordance with the method described in the above embodiment.

3.2. Example 1

5.0 g of hyaluronic acid (molecular weight 8,000, manufactured by Kewpie Corporation) was dissolved in 500 mL of water in a one liter volume of beaker, and then an aqueous solution of 40% of tetrabutylammonium hydroxide was added while stirring, and the pH value was adjusted to 7.2. After the pH adjustment, freeze dehydration was performed to obtain 10.2 g of a tetrabutylammonium hydroxide salt of hyaluronic acid. 1.0 g of the obtained tetrabutylammonium hydroxide salt of hyaluronic acid, 2.0 g of C12 to 13 alkyl glycidyl ether (reaction reagent) (manufactured by Yokkaichi Synthesis Corporation), and 10 mL of dimethylformamide (DMF) are added to a 30 mL volume of sample bottle, and the reaction was performed for eight hours in a water bath at 80° C. while stirring. After completing the reaction, 10 mL of an aqueous solution containing 12.5% of sodium chloride was added, the pH was adjusted to 1.0 with 8% hydrochloric acid aqueous solution. Then, 50 mL of ethanol was added slowly to obtain a suspension. Next, the pH was adjusted to 7.0 with 25% sodium hydroxide aqueous solution to generate a precipitate, and the precipitate was collected by filtration and then was washed three times with 50 mL of 80% ethanol aqueous solution. The obtained precipitation was dried in vacuum at 60° C. to obtain 0.48 g of modified hyaluronic acid (test number 6 in Table 1) comprising the glycerin skeleton-containing group shown by the above general formula (1). The kinetic viscosity of the modified hyaluronic acid (test number 6 in table 1) obtained in Example 1 was 1.2 mm$^2$/s.

According to Table 1, since the modified hyaluronic acid of the invention (test numbers 1 to 13) comprises the glycerin skeleton-containing group shown by the above general formula (1), the modified hyaluronic acid of the invention has excellent in solubility in water and ethanol. In particular, the modified hyaluronic acid (test numbers 3 to 9 and 11 to 13) having the number of carbon atoms of the $R^1$ in the glycerin skeleton-containing group of 6 to 20 and the number of the glycerin skeleton-containing group contained in one constitution unit of hyaluronic acid of 0.001 to 0.5 was more excellent in solubility in water and ethanol.

In contrast, since the modified hyaluronic acid of the comparative examples (test numbers 14 and 15) do not comprise the glycerin skeleton-containing group shown by the above general formula (1), the modified hyaluronic acid of the comparative examples has inferior solubility in water and ethanol.

TABLE 1

| | test number | reaction reagent | number of carbon atoms of R1 or palmytol group | solvent | amount of reaction reagent (g) | reaction temperature (° C.) | reaction time (hour) | N | transmittance X of the above-described light in water containing 1 mass % of modified hyaluronic acid | transmittance Y of the above-described light in ethanol-water mixed liquid containing 1 mass % of modified hyaluronic acid |
|---|---|---|---|---|---|---|---|---|---|---|
| Examples | test number 1 | alkyl | 4 | DMF | 1.0 | 80 | 8 | 0.05 | 100% | 22% |
| | test number 2 | glycidyl | 12 to 13 | DMF | 0.05 | 4 | 1 | 0.0006 | 100% | 32% |
| | test number 3 | ether | 12 to 13 | DMF | 0.1 | 20 | 1 | 0.001 | 100% | 55% |
| | test number 4 | | 12 to 13 | DMF | 0.2 | 40 | 2 | 0.006 | 100% | 84% |
| | test number 5 | | 12 to 13 | DMF | 0.4 | 60 | 4 | 0.01 | 100% | 94% |
| | test number 6 | | 12 to 13 | DMF | 2.0 | 80 | 8 | 0.05 | 100% | 100% |
| | test number 7 | | 12 to 13 | DMSO | 2.0 | 80 | 8 | 0.10 | 100% | 100% |
| | test number 8 | | 12 to 13 | none | 20 | 80 | 8 | 0.20 | 42% | 54% |
| | test number 9 | | 12 to 13 | none | 20 | 100 | 24 | 0.46 | 28% | 47% |
| | test number 10 | | 12 to 13 | none | 20 | 120 | 24 | 0.53 | 21% | 38% |
| | test number 11 | | 16 | DMSO | 2.0 | 80 | 8 | 0.05 | 81% | 95% |
| | test number 12 | | 18 | DMF | 2.0 | 80 | 8 | 0.03 | 94% | 92% |
| | test number 13 | | 18 | DMSO | 2.0 | 80 | 8 | 0.05 | 62% | 64% |
| Comparative | test number 14 | palmitoyl | 16 | DMF | 0.8 | 80 | 8 | 0.01 | 45% | 13% |
| Examples | test number 15 | chloride | 16 | DMF | 4.0 | 80 | 8 | 0.03 | 13% | 24% |

FIG. 1A shows 1H-NMR spectrum (observing frequency 400 MHz, internal standard substance: DSS (0 ppm), solvent: deuterium oxide) of the modified hyaluronic acid obtained in this Example. In contrast, as a comparative control, FIG. 1B shows 1H-NMR spectrum (observing frequency 400 MHz, internal standard substance: DSS (0 ppm), solvent: deuterium oxide) of a source hyaluronic acid (without a glycerin skeleton-containing group) (manufactured by Kewpie Corporation, average molecular weight 8,000). The peak appearing at about 1.3 ppm is considered to be a peak representing protons of a methylene group (—CH$_2$—) in the glycerin skeleton-containing group of the modified hyaluronic acid.

Additionally, each of the modified hyaluronic acid of test numbers 1 to 5 and 7 to 15 in Table 1 was manufactured in the similar method to Example 1 except the reagent types, the solvent, the reaction temperature, and the reaction time were modified as shown in Table 1. The modified hyaluronic acid having the number of carbon atoms in the $R^1$ of the glycerin skeleton-containing group shown in Table 1 was obtained by changing the reagent types. Furthermore, the introduction of the glycerin skeleton-containing group in the obtained modified hyaluronic acid in Table 1 was confirmed from 1H-NMR spectrum, in accordance with the similar method to the above-described method. The kinetic viscosity of the modified hyaluronic acid of test numbers 1 to 15 was also 0.5 to 3 mm$^2$/s.

3.3. Example 2

Modified hyaluronic acid was manufactured by the similar method to Example 1 except hyaluronic acid (molecular weight 300,000, manufactured by Kewpie Corporation) was used in place of hyaluronic acid (molecular weight 8,000, manufactured by Kewpie Corporation) in the method of manufacturing the modified hyaluronic acid of Example 1. The introduction of the glycerin skeleton-containing group in the modified hyaluronic acid obtained in Example 2 was also confirmed from 1H-NMR spectrum, in accordance with the similar method to the above-described method.

The number of the glycerin skeleton-containing group in one constitution unit of hyaluronic acid in the modified hyaluronic acid obtained in Example 2 was 0.03, and the transmittance X of the above-mentioned light in water containing 1% of modified hyaluronic acid was 100%, and transmittance Y of the above-mentioned light in ethanol-water mixed liquid (ethanol content: 70 vol %) containing 1% of modified hyaluronic acid was 100%. The kinetic viscosity of the modified hyaluronic acid obtained in Example 2 was also 3.5 mm$^2$/s.

3.4. Example 3

5.0 g of hyaluronic acid (molecular weight 1,000,000, manufactured by Kewpie Corporation) was dissolved in 500 mL of water in a one liter volume of beaker, and then an aqueous solution of 40% of tetrabutylammonium hydroxide was added while stirring, and the pH value was adjusted to 7.2. After the pH adjustment, freeze dehydration was performed to obtain 10.2 g of a tetrabutylammonium hydroxide of hyaluronic acid. 1.0 g of the obtained tetrabutylammonium hydroxide of hyaluronic acid, 2.0 g of C 12 to alkyl glycidyl ether (reaction reagent) (manufactured by Yokkaichi Synthesis Corporation), and 20 mL of dimethylformamide (DMF) are added to a 30 mL volume of sample bottle, and the reaction was performed for eight hours in a water bath at 80° C. while stirring. After completing the reaction, 10 mL of an aqueous solution containing 12.5% of sodium chloride was added, the pH was adjusted to 7.0 with 25% sodium hydroxide aqueous solution, and then 50 mL of ethanol was added slowly to precipitate hyaluronic acid. Next, the precipitate was collected by filtration and then was washed three times with 50 mL of 80% ethanol aqueous solution. The obtained precipitation was dried in vacuum at 60° C. to obtain modified hyaluronic acid. The introduction of the glycerin skeleton-containing group in the modified hyaluronic acid obtained in Example 3 was also confirmed from 1H-NMR spectrum, in accordance with the similar method to the above-described method.

The number of the glycerin skeleton-containing group in one constitution unit of hyaluronic acid in the modified hyaluronic acid obtained in Example 3 was 0.02, and the transmittance X of the above-mentioned light in water containing 1% of modified hyaluronic acid was 100%, and transmittance Y of the above-mentioned light in ethanol-water mixed liquid (ethanol content: 70 vol %) containing 1% of modified hyaluronic acid was 75%. The kinetic viscosity of the modified hyaluronic acid obtained in Example 3 was also 46 mm$^2$/s.

3.5. Test Example 1

In this test example, a lotion containing the modified hyaluronic acid obtained in Example 1 was prepared according to the following formulation.
modified hyaluronic acid (Example 1) 0.2%
sodium hyaluronate 0.1%
hydrolyzed hyaluronic acid 0.1%
collagen peptide 0.1%
1,3-butylene glycol 5.0%
glycerin 3.0%
isostearyl alcohol 0.1%
tocopherol acetate 0.1%
POE(20) sorbitan monolaurylate 0.5%
POE(15) lauryl alcohol ether 0.5%
pyrrolidone carboxylic acid zinc 0.1%
ethylparaben 0.1%
methylparaben 0.15%
ethanol 5.0%
essence proper quantity
purified water balance

3.6. Test Example 2

In this test example, a milky lotion containing the modified hyaluronic acid obtained in Example 1 was prepared according to the following formulation.
modified hyaluronic acid (Example 1) 0.3%
pentylene glycol 5.0%
glycerin 3.0%
squalane 5.0%
stearic acid 0.5%
stearyl alcohol 2.0%
vaseline 4.0%
stearic acid sorbitan 1.0%
POE(10) monostearate 1.0%
carboxyvinyl polymer 0.5%
poly cotanium-51 0.1%
methylparaben 0.15%
propylparaben 0.1%
potassium hydroxide 0.1%
BHT 0.02%
sodium EDTA-2 0.02%
essence proper quantity
purified water balance

3.7. Test Example 3

In this test example, cream (emollient cream) containing the modified hyaluronic acid obtained in Example 2 was prepared according to the following formulation.
modified hyaluronic acid (Example 2) 0.5%
polyethylene glycol 4.0%
1,3-propanediol 6.0%
squalane 11.0%
dimethicone 1.0%
cetanol 6.0%
stearic acid 2.0%
hydrogenated cocoglyceryl 4.0%
tricaprylin 8.0%
glyceryl monostearate 3.0%
POE(20) cetyl alcohol ether 2.0%
coenzyme Q10 0.03%
ceramide 0.1%
sodium lysine dilauroyl glutamate 0.1%
sodium EDTA-2 0.02%
propylparaben 0.1%
methylparaben 0.15%
essence proper quantity
purified water balance

3.8. Test Example 4

In this test example, beauty essence (whitening and moisture essence) containing the modified hyaluronic acid obtained in Example 2 was prepared according to the following formulation.
modified hyaluronic acid (Example 2) 0.8%
sodium hyaluronate 0.2%
hydrolyzed hyaluronic acid 0.1%
1,3-butyleneglycol 5.0%
glycerin 1.5%
POE sorbitan monostearate 1.0%
sorbitan monostearic acid ester 0.5%
xanthane gum 0.2%
sodium alginate 0.2%
carboxyvinyl polymer 0.2%
potassium hydroxide 0.1%
olive oil 0.2%
tocopherol 0.1%
sodium EDTA-2 0.02%
arginine 0.15%
dipotassium glycyrrhizinate 0.05%
arbutin 0.2%
retinol palmitate 0.2%
ku shen extract 0.2%
marine algae extract 0.2%
tranexamic acid 0.1%
elastin 0.1%
collagen 0.1% magnesium phosphoric acid ascorbate 0.1%
sodium citrate 1.0%
citric acid 0.1%
propyl paraben 0.1%
methylparaben 0.15%
essence proper quantity
purified water balance

3.9. Test Example 5

In this test example, beauty essence pack (pasty peel-off type) containing the modified hyaluronic acid obtained in Example 1 was prepared according to the following formulation.
modified hyaluronic acid (Example 1) 0.5%
poly vinyl acetate emulsion 17.0%
poly vinylalcohol 11.0%
sorbitol 5.0%
polyethylene glycol 400 5.0%
squalane 2.5%
POE sorbitan monostearate 1.0%
titanium oxide 4.0%
talc 8.0%
ethanol 8.0%
methylparaben 0.15%
essence proper quantity
purified water balance

3.10. Test Example 6

In this test example, facial wash (cleansing foam) containing the modified hyaluronic acid obtained in Example 1 was prepared according to the following formulation.
modified hyaluronic acid (Example 1) 0.2%
cationized hyaluronic acid 0.1%
(manufactured by Kewpie corporation, brand name "Hyaloveil")
glycerin 10.0%
poly ethylene glycol 400 15.0%
dipropylene glycol 10.0%
sodium lauroyl glutamate 20.0%
POE(2) monostearate 5.0%
sodium palm fatty acid glutamate 8.0%
alkyl betaine 2.0%
sodium EDTA-2 0.02%
propylparaben 0.1%
methylparaben 0.15%
essence proper quantity
purified water balance

3.11. Test Example 7

In this test example, sunscreen preparation (milky lotion) containing the modified hyaluronic acid obtained in Example 1 was prepared according to the following formulation.
modified hyaluronic acid (Example 1) 0.2%
1,3-butyleneglycol 3.0%
dipropylene glycol 3.0%
cyclo methicone 5.0%
dimethicone 5.0%
cetanol 1.0%
vaseline 1.0%
octyl methoxycinnamate 5.0%
titanium oxide 2.0%
zinc oxide 2.0%
stearic acid sorbitan 1.0%
POE(20) sorbitan monostearate 1.0%
phenoxyethanol 0.8%
methylparaben 0.1%
essence proper quantity
purified water balance

3.12. Test Example 8

In this test example, lip balm containing the modified hyaluronic acid obtained in Example 1 was prepared according to the following formulation.
modified hyaluronic acid (Example 1) 0.1%
microcrystalline wax 1.5%
ceresin 12.0%
squalane 10.0%
decamethyltetrasiloxane 10.0%
diisostearyl maleate 5.0%
candelilla wax 2.0%
vaseline 8.0%
glyceryl hydroxystearate 2.0%
menthol 0.05%
liquid paraffin 1.0%
tocopherol acetate 0.1%
tocopherol 0.05%
propylparaben 0.1%
essence proper quantity
purified water balance

3.13. Test Example 9

In this test example, shampoo containing the modified hyaluronic acid obtained in Example 1 was prepared according to the following formulation.
modified hyaluronic acid (Example 1) 0.2%
cationized hyaluronic acid 0.1%
(manufactured by Kewpie corporation, brand name "Hyaloveil")
POE(20) lauryl ether sodium sulfonate 11.0%
sodium lauroyl aspartate 10.0%
palm oil fatty acid amide propyl betaine 4.0%
palm oil fatty acid mono ethanol amide 2.0%
sodium EDTA-2 0.1%
sodium benzoate 0.2%
phenoxyethanol 0.8%
methylparaben 0.1%
essence proper quantity
purified water balance

3.14. Test Example 10

In this test example, hair conditioner containing the modified hyaluronic acid obtained in Example 1 was prepared according to the following formulation.
modified hyaluronic acid (Example 1) 0.3%
cationized hyaluronic acid 0.2%
(manufactured by Kewpie corporation, brand name "Hyaloveil")
stearyl alcohol 4.0%
cetanol 1.5%
hydroxyethylurea 1.0%
aminopropyldimethicone 1.5%
dimethicone 0.5%
hydrolyzed silk 1.0%
1,3-butyleneglycol 1.0%
glycerin 3.0%
cetyl 2-ethylhexanoate 2.0%
isocetyl myristate 0.4%
L-arginine 0.1% trehalose 0.1%
sorbitol 0.1%
ceratin peptide 0.1%
POE(4) stearate 1.0%
stearic acid dimethyl aminopropyl amide 3.0%
distearyldimethylammonium chloride 0.2%
sodium benzoate 0.3%
phenoxyethanol 0.8%
methylparaben 0.1%
essence proper quantity
purified water balance

3.15. Test Example 11

Confirmation Test of Skin Barrier Function Repair Effect

Process liquid (ceramide II (manufactured by Takasago International Corporation), 4 mg of ceramide III (manufactured by Cosmoferm, Inc), 4 mg of ceramide IV (manufactured by Cosmoferm, Inc), 8 mg of stearic acid (manufactured by Wako Pure Chemical Industries, Ltd.), 8 mg of cholesterol (manufactured by KANTO CHEMICAL CO., INC.), 2 mg of cholesterol sulfate (manufactured by Sigma-Aldrich, Inc), 140 mg of pure water, and 1 mg of the modified hyaluronic acid of each test number of Example 1 were added to 2 mL volume of Eppendorf tube, and the mixture was then stirred with a vortex for two minutes at an ambient temperature. Next, the mixture was heated in a constant-temperature bath at 80° C. for five minutes, and then was stirred with a vortex for two minutes, and then was cooled in a constant-temperature bath at 10° C. for five minutes, and then ultrasonication treatment was performed at an ambient temperature for five minutes. This manipulation was repeated four times to obtain a sample for microscopic observation in accordance with the following procedure.

1 microliter of the above-described sample was applied on apiece of glass slide, and the glass slide was covered with a piece of cover glass, and the sample was spread out entirely under the cover glass to obtain a microscopic observation. Microscopic observation was performed with digital microscope VHX-600 manufactured by Keyence Corporation on polarization observation mode at 1,000 magnification. Five arbitrary observation fields (225×310 micrometers) was selected, taking photographs, the number of black cross-shaped images having a diameter of 5 micrometers or more was counted in the five photographs, and the average number was calculated per one photograph. As a control, the same treatment was also performed by using process liquid without modified hyaluronic acid. The result is shown in Table 2.

TABLE 2

|  | addition of modified hyaluronic acid | | | | absence of modified hyaluronic acid |
| --- | --- | --- | --- | --- | --- |
| test number of modified hyaluronic acid in use | 12 | 13 | 6 | 7 | — |
| number of carbon atoms of R1 | 18 | | 12 to 13 | | — |
| N | 0.03 | 0.05 | 0.05 | 0.10 | — |
| average number of cross-shaped images | 9.8 | 5.6 | 16.2 | 12 | 1 |

Figure 2:
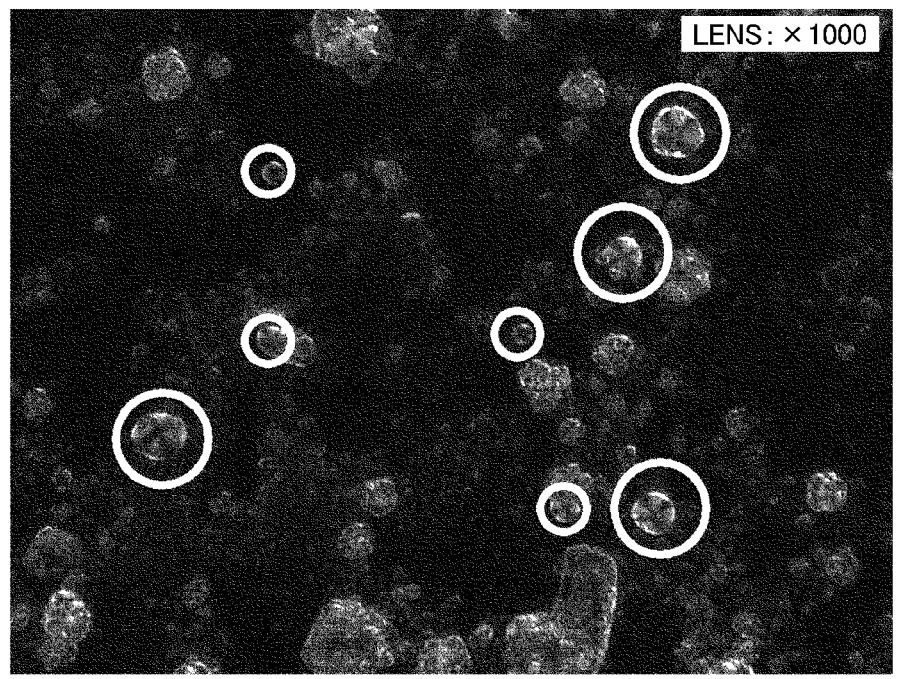
FIG. 2 shows a microscope photograph of a sample obtained in Comparative Example 11.

In FIG. 2, the cross-shaped images (marked by circles) represent a portion in which a lamellar structure is formed. In a corneum of healthy skin, in general, a lipid layer and a water layer constitute a lamellar structure, and the lamellar structure contributes skin barrier function. Accordingly, the more the number of the portions in which the lamellar structure is formed, the higher the repair effect of the skin barrier function is.

According to Table 2, when the process liquid comprises modified hyaluronic acid, the number of the cross-shaped images is more compared with the case when the process liquid does not comprise modified hyaluronic acid. According to the result, it is considered that the modified hyaluronic acid comprising the glycerin skeleton-containing group shown by the general formula (1) has a repair effect of the skin barrier function.

3.16. Test Example 12

Confirmation Test of Repair Effect of Human Skin Barrier Function

In this test example, the modified hyaluronic acid was applied on human skin to evaluate trans-epidermal water loss (TEWL).
3.16.1. Test Method
3.16.1-1. Subjects
Test was performed for nine adults (n=9) having an age of 26 to 34.
3.16.1-2. Samples
Sample 1: The modified hyaluronic acid obtained in the above Example 1
Sample 2 (Control): hyaluronic acid (molecular weight 8,000, manufactured by Kewpie Corporation)
Test liquid 1 was an aqueous solution containing 1% of sample 1, obtained by dissolving sample 1 in purified water. Test liquid 2 was an aqueous solution containing 1% of sample 2, obtained by dissolving sample 2 in purified water.
3.16.1-3. Test Method
Two portions having a diameter of 1 cm were selected from the forearm of the each subject as test portions.

At first, TEWL at the test portions were measured with a device for measuring the amount of water evaporation, brand name "Cutometer MPA580", manufactured by CK-Electronic.

Then, the corneum of the inner side of the forearm was removed by tape-stripping until the values of TEWL became 15 to 25 g/m2·h. In this way, treatment for destructing skin barrier function was performed.

After performing the treatment for destructing skin barrier function, test liquid 1 or test liquid 2 was applied.

The application was performed twice per day, one was performed in the morning, and the other was performed in the afternoon, and the amount of the application was 20 microliter per one time.

The test portions of the subjects were washed before the measurement, keeping the subject at rest for twenty minutes before the measurement.

The measurement was performed at the time of one day in the morning and at the time of three days in the morning from applying the each test liquid followed by performing the treatment for destructing skin barrier function.

Multiple comparison test under Dunnett method was performed on each measurement day for the difference between the TEWL after applying the each test liquid and the TEWL after removing the corneum, and there is a significant difference in the case of p<0.05.

Figure 3:
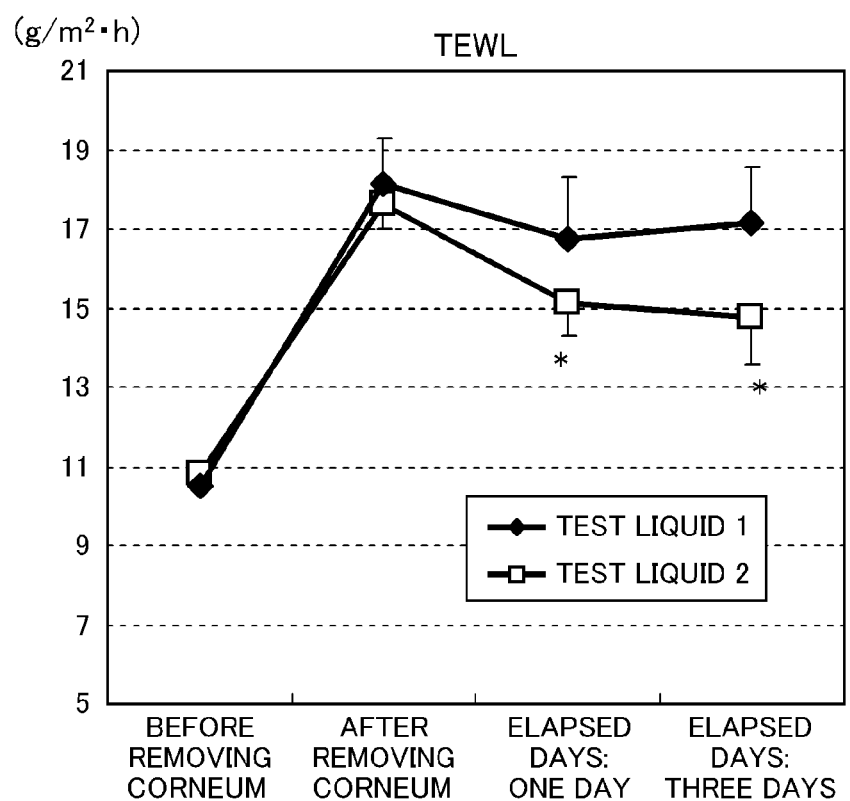
FIG. 3 shows measured values of TEWL when applying test liquid 1 and test liquid 2, respectively.

Table 3 and FIG. 3 show measurement values of TEWL when applying test liquid 1 and test liquid 2, respectively.

Furthermore, in Table 3, the number of value represents an average value of the TEWL measurement values among the subjects.

Figure 4:
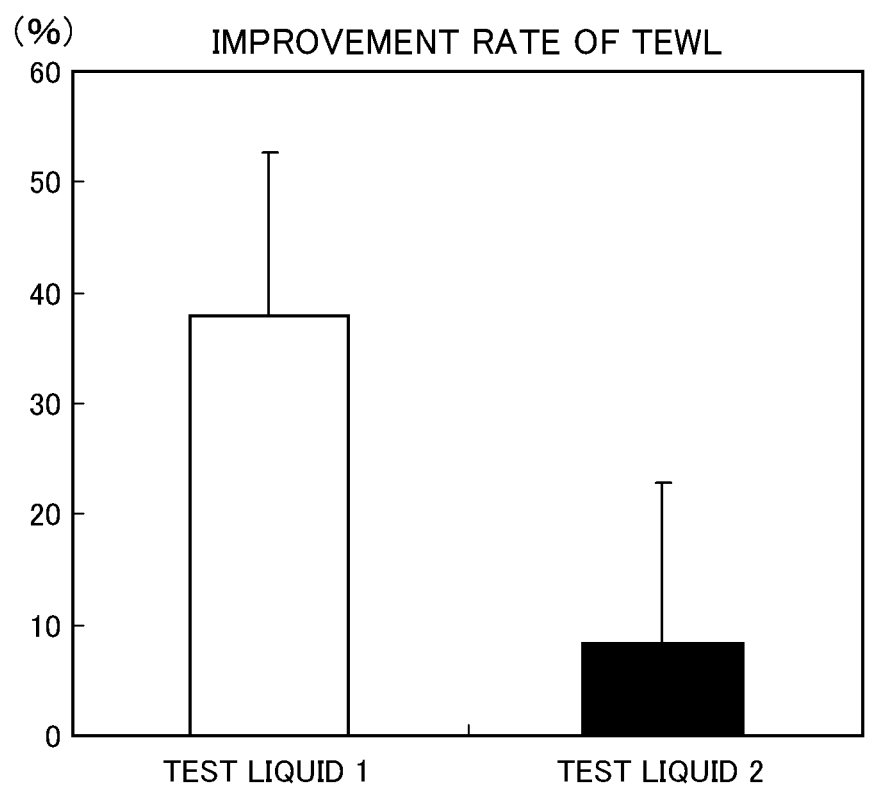
FIG. 4 shows improvement rates (%) at the time of three days from applying test liquid 1 and test liquid 2, respectively.

Additionally, the improvement rate of the TEWL at the time of three days from applying the test liquid was calculated in accordance with the following formula (10). The each improvement rate (%) at the time of three days from applying the test liquid 1 and test liquid. 2 respectively in Table 3 is shown in FIG. 4.

Improvement Rate (%)=100×{1−[(TEWL at the time of three days from the application−TEWL before removing corneum)/(TEWL at immediately after removing corneum−TEWL before removing corneum)]}   (10)

TABLE 3

| | TEWL [g/m² · h] | | | | |
|---|---|---|---|---|---|
| | before removing corneum | immediately after removing corneum | at the time of one day from application | at the time of three days from application | improvement rate (%) at the time of three days from application |
| test liquid 1 | 10.8 | 17.6 | 15.1* | 14.8* | 37.9 |
| test liquid 2 | 10.5 | 18.1 | 16.8 | 17.2 | 8.2 |

In Table 3 and FIG. 3, TEWL represents the amount of water transfer from inside the skin to outward. If the lamellar structure of the corneum is destroyed by the treatment for destructing skin barrier function, the value of the TEWL increases. Accordingly, in this test example, the lower the TEWL is, the higher the repair effect of the skin barrier function is.

According to Table 3 and FIG. 3, when the test liquid 1 was applied, the value of the TEWL decreases, compared with the case when the test liquid 2 was applied.

Additionally, when the test liquid 1 was applied, the TEWL after applying the test liquid 1 showed a significant difference at the time of one day and three days from applying the test liquid 1.

Further, according to Table 3, when the test liquid 1 was applied, the improvement rate of the TEWL is higher, compared with the case when the test liquid 2 was applied.

According to this result, it is considered that the modified hyaluronic acid comprising the glycerin skeleton-containing group shown by the general formula (1) has an excellent repair effect of the skin barrier function.

3.17. Test Example 13

Solubility Test 0.1 g of the following sample A was added to 10 mL of ethanol-water mixed liquid having the volume ratio of ethanol:water=70:30 to prepare water containing 1% of modified hyaluronic acid. Similarly, another water containing 1% of modified hyaluronic acid was prepared by using the following sample B instead of the sample A.

sample A: modified hyaluronic acid obtained in the above Example 1 sample B (Control): hyaluronic acid (molecular weight 8,000, manufactured by Kewpie Corporation)

As a result, the water containing 1% of modified hyaluronic acid, which was prepared with using the sample A, was transparent by naked eyes and precipitation was not confirmed. From the result, the modified hyaluronic acid was almost dissolved in the water containing 1% of the modified hyaluronic acid, which was prepared with using the sample A. The water containing 1% of the modified hyaluronic acid, which was prepared with using the sample A, for example, can be used as a raw material for a cosmetic preparation containing an oily raw material.

In contrast, although turbidity was not confirmed by naked eyes in the water containing 1% of the modified hyaluronic acid, which was prepared with using the sample B, precipitation was confirmed at the bottom of the container in which the water was contained.

According to the result, it is considered the modified hyaluronic acid comprising the glycerin skeleton-containing group shown by the general formula (1) can be suitably used for a cosmetic preparation having high hydrophobicity.

The embodiment of the invention has been explained as set out above. The invention includes substantially the same component as a component explained in the embodiment (for example, a component having the same function, the same method, and the same result, or a component having the same object and the same result). Also, the invention includes a component, a non-essential part explained in the embodiment of which is replaced with others. Additionally, the invention includes a component having the same effect as a component explained in the embodiment, or a component which can achieve the same object as a component explained in the embodiment. Further, the invention includes a component obtained by adding a heretofore known technology to a component explained in the embodiment.

The invention claimed is:

1. A modified hyaluronic acid and/or a salt thereof comprising a glycerin skeleton-containing group shown by the following general formula (1),

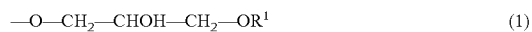
—O—CH₂—CHOH—CH₂—OR¹   (1)

wherein, $R^1$ represents a linear or branched alkyl group, or a linear or branched alkenyl group, and the glycerin skeleton-containing group is bonded to a carbonyl group of a hyaluronic acid skeleton.

2. The modified hyaluronic acid and/or a salt thereof according to claim 1, the $R^1$ in the general formula (1) is a linear or branched alkyl group which has 6 to 20 carbon atoms, or a linear or branched alkenyl group which has 6 to 20 carbon atoms.

3. The modified hyaluronic acid and/or a salt thereof according to claim 1, wherein the $R^1$ is selected from the group consisting of n-dodexyl, n-tridecyl, n-tetradecyl, n-hexadecyl, n-octadecyl, and n-icocyl.

4. The modified hyaluronic acid and/or a salt thereof according to claim 1, obtained by reacting a hyaluronic acid and/or a salt thereof having a molecular weight of 2,000 to 50,000 with a compound shown by the following general formula (2) in an organic solvent,

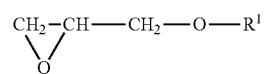

wherein, $R^1$ represents a linear or branched alkyl group having 12 to 20 carbon atoms, or a linear or branched alkenyl group having 12 to 20 carbon atoms.

5. The modified hyaluronic acid and/or a salt thereof according to claim 1, a number of the glycerin skeleton-containing group in one hyaluronic acid constituent unit is 0.001 to 0.5.

6. The modified hyaluronic acid and/or a salt thereof according to claim 1, the number of the glycerin skeleton-containing groups in one hyaluronic acid constituent unit is 0.001 to 0.2.

7. The modified hyaluronic acid and/or a salt thereof according to claim 1, the number of the glycerin skeleton-containing groups in one hyaluronic acid constituent unit is 0.01 to 0.15.

8. The modified hyaluronic acid and/or a salt thereof according to claim 1, wherein a kinetic viscosity (1 mass % aqueous solution) of the modified hyaluronic acid and/or a salt thereof is 50 mm$^2$/s or less.

9. The modified hyaluronic acid and/or a salt thereof according to claim 1, wherein a transmittance X defined in the following formula (i) is 40% or more, and
wherein a transmittance Y defined in the following formula (ii) is 50% or more:

$$X = T2/T1 \times 100\ (\%) \qquad (i),$$

wherein T1 is a transmittance of light having a wavelength of 660 nm and a light path length of 10 mm in water, and T2 is a transmittance of light having a wavelength of 660 nm and a light path length of 10 mm in water comprising 1% of the modified hyaluronic acid and/or a salt thereof comprising the glycerin skeleton-containing group, $$Y = T4/T3 \times 100\ (\%) \qquad (ii),$$

wherein T3 is a transmittance of light having a wavelength of 660 nm and a light path length of 10 mm in an ethanol-water mixed liquid comprising 70 vol % of ethanol, and T4 is a transmittance of light having a wavelength of 660 nm and a light path length of 10 mm in an ethanol-water mixed liquid comprising 70 vol % of ethanol, which comprises 1% of the modified hyaluronic acid and/or a salt thereof comprising the glycerin skeleton-containing group.

10. The modified hyaluronic acid and/or a salt thereof according to claim 9, wherein the transmittance X is 80% or more.

11. The modified hyaluronic acid and/or a salt thereof according to claim 9, wherein the transmittance Y is 80% or more.

12. A cosmetic preparation comprising the modified hyaluronic acid and/or a salt thereof according to claim 1.

13. The cosmetic preparation according to claim 12, further comprising an oily material.

14. The cosmetic preparation according to claim 12, further comprising an alcohol.

15. The cosmetic preparation according to claim 12, further comprising water.

16. A method for manufacturing the modified hyaluronic acid and/or a salt thereof according to claim 1 comprising reacting a hyaluronic acid and/or a salt thereof with a compound shown by the following general formula (2),

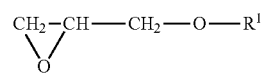

(2)

wherein, R$^1$ represents a linear or branched alkyl group, or a linear or branched alkenyl group.

* * * * *